United States Patent
Hohla

(10) Patent No.: US 7,022,119 B2
(45) Date of Patent: Apr. 4, 2006

(54) EXCIMER LASER EYE SURGERY SYSTEM

(75) Inventor: Kristian Hohla, Vaterstetten (DE)

(73) Assignee: Technolas GmbH Ophthalmologische Systeme, Munich (DE)

( * ) Notice: Subject to any disclaimer, the term of this patent is extended or adjusted under 35 U.S.C. 154(b) by 0 days.

(21) Appl. No.: 10/424,337

(22) Filed: Apr. 25, 2003

(65) Prior Publication Data

US 2003/0225400 A1 Dec. 4, 2003

Related U.S. Application Data

(60) Continuation of application No. 09/777,626, filed on Feb. 6, 2001, now abandoned, which is a division of application No. 09/288,732, filed on Apr. 9, 1999, now abandoned, which is a continuation of application No. 08/656,856, filed on May 30, 1996, now abandoned.

(51) Int. Cl.
 *A61F 9/008* (2006.01)
(52) U.S. Cl. ............... 606/10; 606/5; 606/13
(58) Field of Classification Search ........... 606/4, 606/5, 6, 10–14, 17, 166, 167, 180–183
 See application file for complete search history.

(56) References Cited

U.S. PATENT DOCUMENTS

| | | | |
|---|---|---|---|
| 4,554,917 A | | 11/1985 | Tagnon |
| 4,638,801 A | * | 1/1987 | Daly et al. ............ 606/4 |
| 4,665,913 A | | 5/1987 | L'Esperance, Jr. |
| 4,669,466 A | * | 6/1987 | L'Esperance ............ 606/5 |
| 4,721,379 A | | 1/1988 | L'Esperance |
| 4,729,372 A | | 3/1988 | L'Esperance, Jr. |
| 4,732,148 A | | 3/1988 | L'Esperance, Jr. |
| 4,840,175 A | | 6/1989 | Peyman |
| 4,856,513 A | | 8/1989 | Muller |
| 4,881,808 A | | 11/1989 | Bille et al. |
| 4,901,718 A | | 2/1990 | Bille et al. |
| 4,902,122 A | | 2/1990 | Azema et al. |
| 4,902,123 A | | 2/1990 | Yoder, Jr. |
| 4,903,695 A | | 2/1990 | Warner et al. |
| 9,903,695 | * | 2/1990 | Warner et al. ............ 606/5 |
| 4,911,711 A | | 3/1990 | Telfair et al. |
| 4,923,467 A | | 5/1990 | Thompson |
| 4,941,093 A | | 7/1990 | Marshall et al. |
| 4,973,330 A | | 11/1990 | Azeman et al. |
| 4,993,826 A | | 2/1991 | Yoder |
| 4,994,058 A | | 2/1991 | Raven et al. |
| 4,998,819 A | | 3/1991 | Labinger et al. |
| 5,098,426 A | | 3/1992 | Sklar et al. |
| 5,106,183 A | | 4/1992 | Yoder |
| 5,137,530 A | | 8/1992 | Sand |
| 5,147,352 A | | 9/1992 | Azema et al. |
| 5,240,553 A | | 8/1993 | Jones ............ 156/643 |
| 5,295,989 A | * | 3/1994 | Nakamura ............ 606/16 |

(Continued)

FOREIGN PATENT DOCUMENTS

DE  3737410  5/1989

(Continued)

*Primary Examiner*—David M. Shay

(57) ABSTRACT

A compact excimer laser system is provided that includes argon fluoride laser gas, electronic, and laser head all compactly arranged such that the patient bed can rotate over all of these components. This allows the patient bed to be rotated for easy egress of the patient without striking the head against an optical extension through which the excimer laser is fired onto the patient's eye. Further, an automated lamellar keratoplasty system is incorporated into the electronics and components of the laser system so that laser in situ keratomileusis can be easily performed.

6 Claims, 5 Drawing Sheets

U.S. PATENT DOCUMENTS

| | | |
|---|---|---|
| 5,374,265 A | 12/1994 | Sand |
| 5,404,884 A | 4/1995 | Lempert |
| 5,460,627 A | 10/1995 | O'Donnell, Jr. |
| 5,496,339 A | 3/1996 | Koepnick |
| 5,548,352 A | 8/1996 | Dewey .................. 351/160 H |
| 5,591,185 A * | 1/1997 | Kilmer et al. .............. 600/166 |
| 5,795,351 A | 8/1998 | Clapham ...................... 606/5 |
| 5,891,132 A | 4/1999 | Hohla ......................... 606/10 |

FOREIGN PATENT DOCUMENTS

| | | |
|---|---|---|
| EP | 111060 | 6/1984 |
| EP | 151869 | 6/1985 |
| EP | 191688 | 8/1986 |
| EP | 207648 | 1/1987 |
| EP | 209992 | 1/1987 |
| EP | 224322 | 6/1987 |
| EP | 247260 | 12/1987 |
| EP | 257836 | 3/1988 |
| EP | 274205 | 7/1988 |
| EP | 299836 | 1/1989 |
| EP | 346116 | 12/1989 |
| EP | 503802 | 9/1992 |
| EP | 628298 | 12/1994 |
| EP | 721129 | 7/1996 |
| FR | 2680677 | 3/1993 |
| WO | WO/90/09141 | 8/1990 |
| WO | WO/95/27534 | 10/1995 |

* cited by examiner

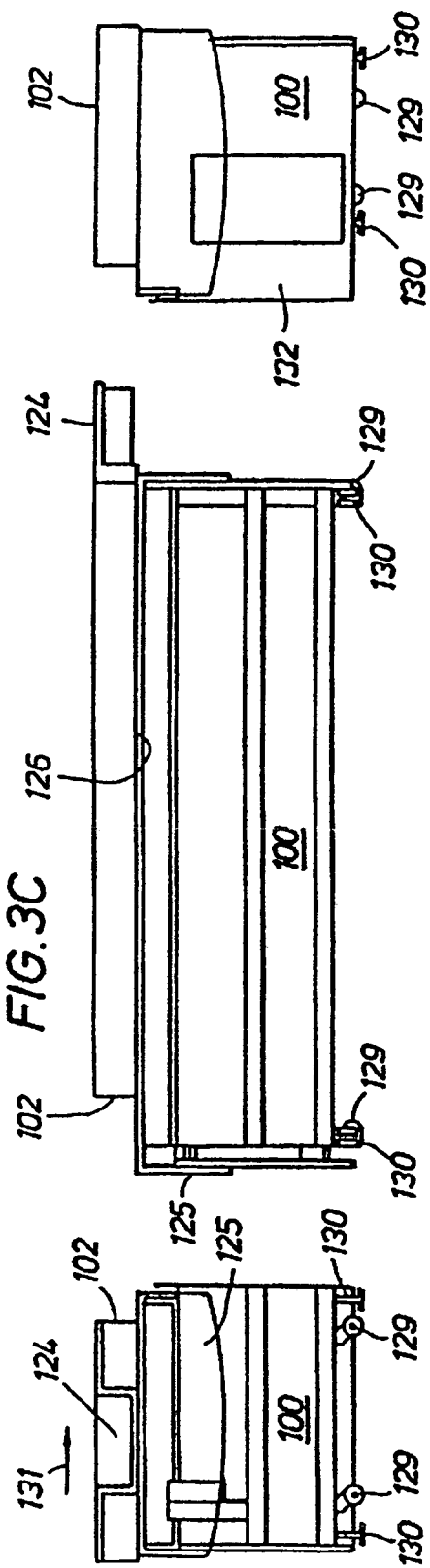
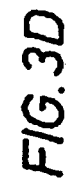
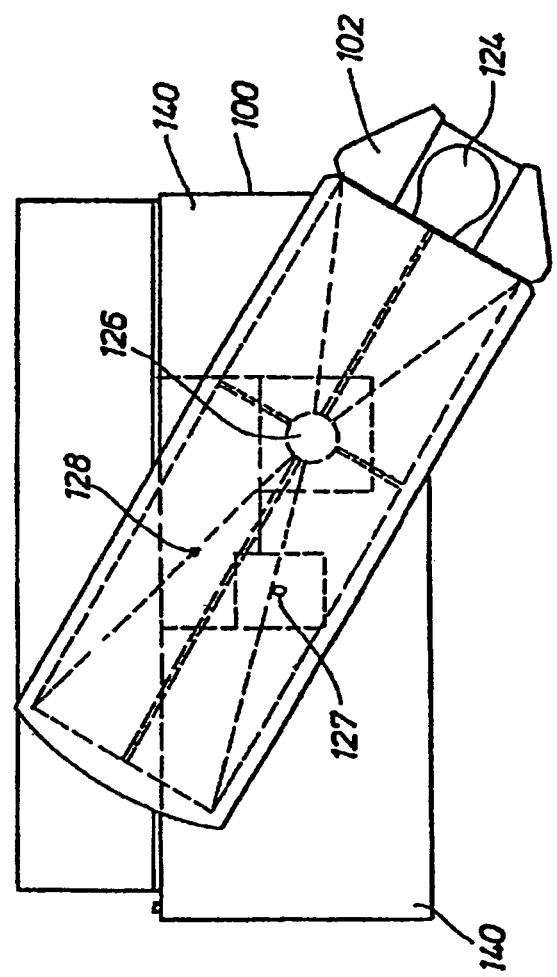
FIG.3D
FIG.3C
FIG.3B
FIG.3A

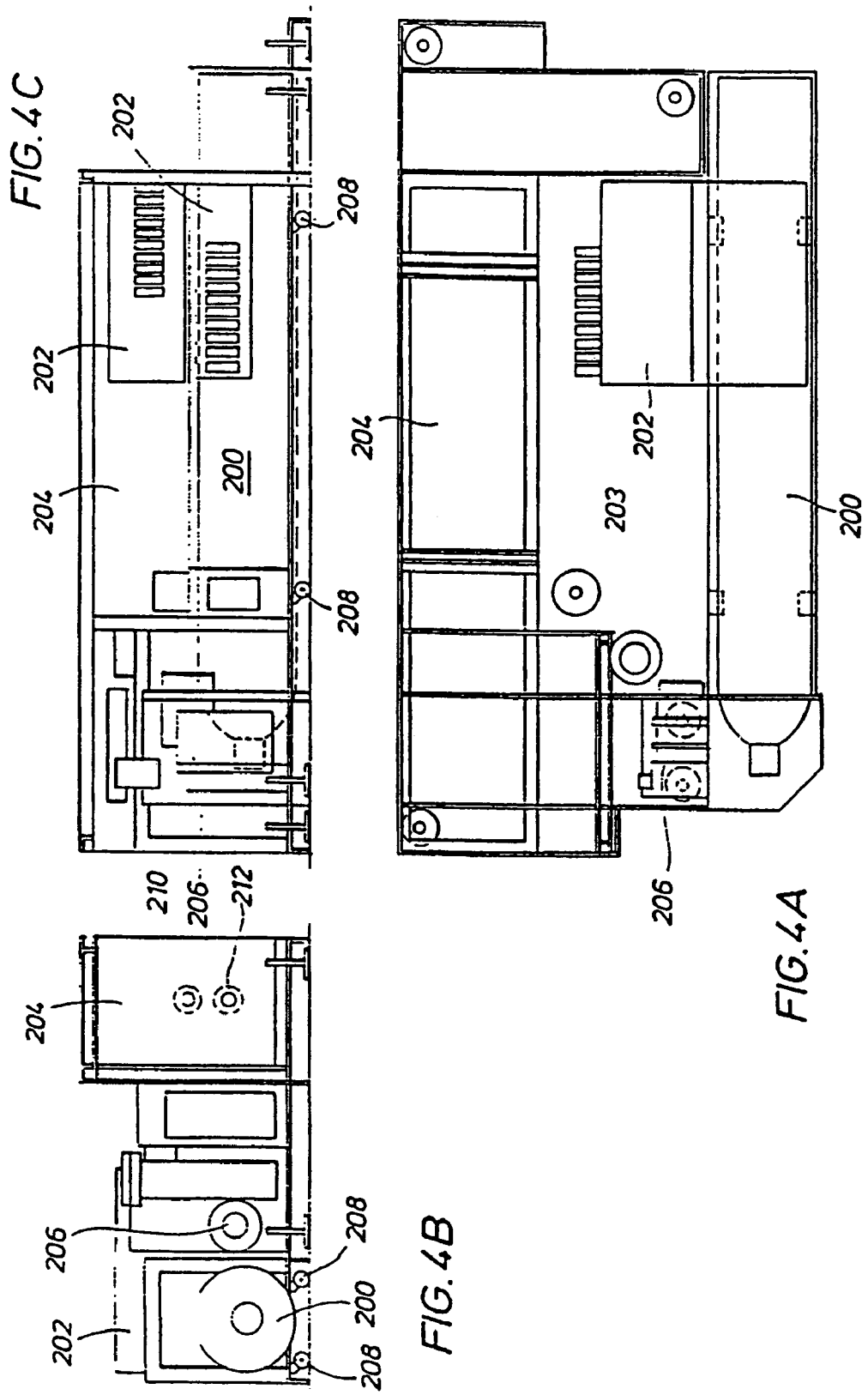

EXCIMER LASER EYE SURGERY SYSTEM

BACKGROUND OF THE INVENTION

1. Field of the Invention

The invention relates to laser systems for eye surgery, and more particularly to a compact excimer laser eye surgery system particularly suited for laser in situ keratomileusis.

2. Description of the Related Art

Since the invention of spectacles, doctors and scientists have striven to improve human vision. From eye glasses, to contact lenses, to radial keratotomy, doctors have sought more convenient and permanent solutions to defective vision.

The development of the excimer laser provided a unique opportunity for vision correction. The excimer laser, especially an argon fluoride excimer laser operating at a 193 nanometers, removes tissue through a non-thermal process of "ablation" in which the molecular bonds of tissue are literally broken. This allows precise amounts of tissue to be removed without heating the surrounding tissue-heating that can burn that tissue leading to scarring. This ablative process using the excimer laser has been employed in a number of ways to literally reprofile the surface of the eye. These techniques are described, for example, in Assignee's U.S. patent application Ser. No. 08/338,495, filed Nov. 16, 1994, and Ser. No. 08/324,782, filed Oct. 18, 1994, which are hereby incorporated by reference.

These techniques have been taken a step further through the development of laser in situ keratomileusis (LASIK), a technique in which the surface layer of the eye is resected, and the underlying stromal tissue is removed using this laser ablation technique. That surface layer is then replaced, and the epithelium then regrows, holding the surface layer in place. This technique has been patented by Gholam Peyman in U.S. Pat. No. 4,840,175, which is hereby incorporated by reference.

Both of these techniques, however, benefit from efficient and compact workstations. These techniques generally should be performed in surgical quality clean rooms. Such clean rooms tend to be expensive, so any reduction in the amount of space taken by an excimer laser surgery system would be beneficial. Further, devices providing an integration of functionality and an increase in efficiency are also greatly desirable.

SUMMARY OF THE INVENTION

Therefore, according to the invention, an excimer laser system is constructed in a highly compact form, in which a patient bed forms an enclosure in which is placed the gas bottle for the excimer laser system, typically holding argon fluoride gas, along with electronics for powering and controlling the excimer laser system. Further, the patient bed enclosure can preferably be rolled away to allow easy access to these components for maintenance and service.

The laser head is placed immediately adjacent to the bed, but below the height of the bed. The bed includes a bearing, allowing the bed to rotate over the laser head and away from an excimer laser optical extension through which the laser beam is fired into the patient's eye. This allows the patient to sit up without striking his or her head. Further, the bed can be rotated 90°, allowing non-laser ophthalmic surgery to be performed using the same equipment in the same clean room.

Further according to the invention, an automated lamellar keratoplasty (ALK) system is integrated into the laser system, providing both computer and monitoring and connections for a microkeratome. Two foot switches are provided, one for advancing and retracting the microkeratome, and the other for activating the vacuum to the microkeratome. This integrated system allows an easily used and controlled system for performing laser in situ keratomileusis (LASIK).

BRIEF DESCRIPTION OF THE DRAWINGS

A better understanding of the present invention can be obtained when the following detailed description of the preferred embodiment is considered in conjunction with the following drawings, in which:

FIGS. 3A–D are top, front, back, and side views of the patient bed enclosure and rotatable patient bed according to the invention;

FIGS. 4A–C are top, front, and side views of the equipment enclosed by the patient bed enclosure of FIGS. 3A–D.

DETAILED DESCRIPTION OF THE PREFERRED EMBODIMENT

Figure 1:
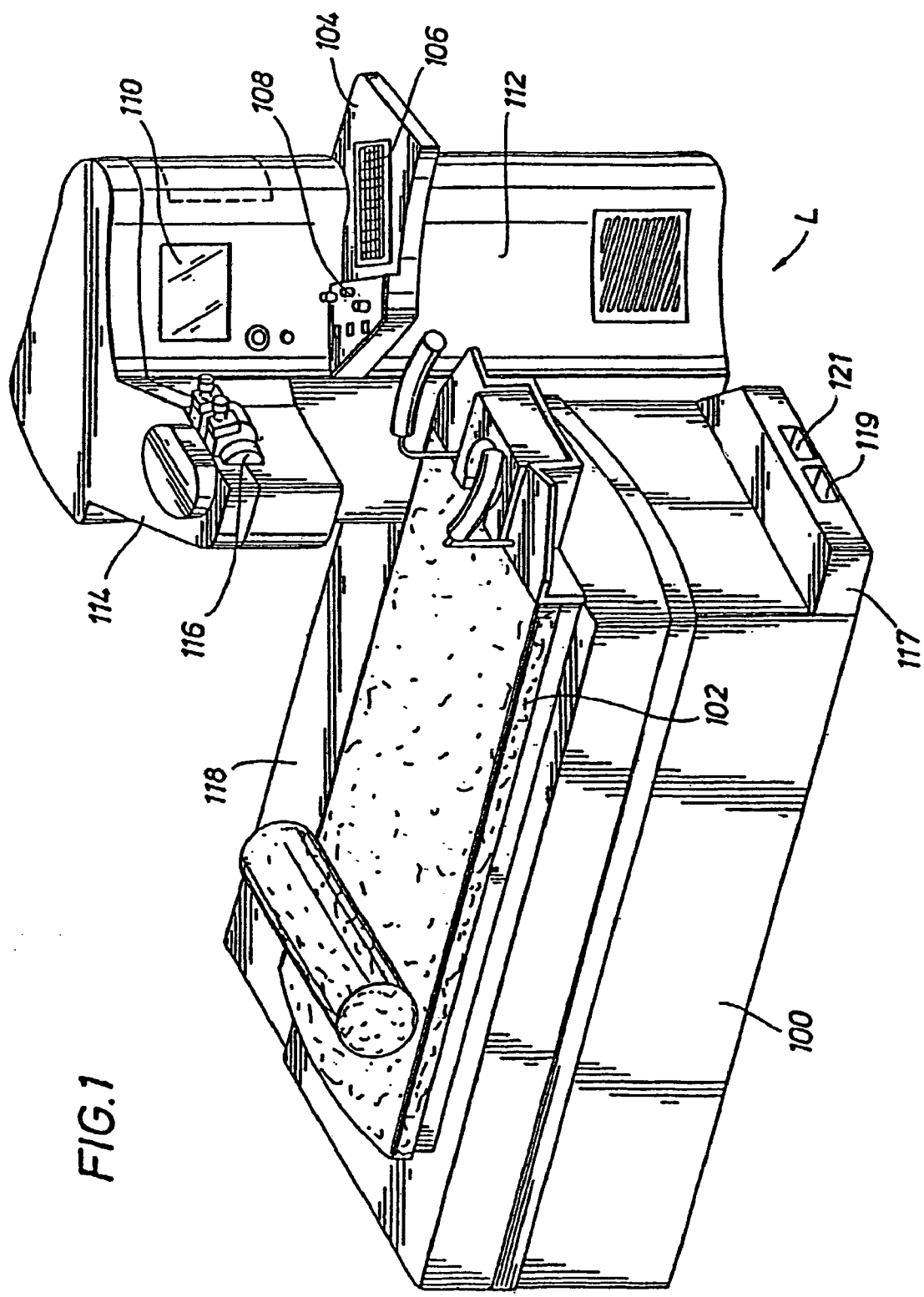
FIG. 1 is a perspective view of the laser system according to the invention.

Turning to FIG. 1, shown is the laser system L according to the invention. This laser system is preferably based on a 193 nm argon-fluoride excimer laser, but other lasers could be used. A patient bed enclosure 100 includes a patient bed 102 disposed on top of it. A physician workstation platform 104 is situated diagonally away from the patient bed 102, and includes a keyboard 106 and control inputs 108. The keyboard 106 and control inputs 108 provide input to a computer system that in part controls the laser system L. That computer system provides data for a display 110. The control inputs 108, the keyboard 106, and the display 110, all in conjunction with the computer system, serve to control the laser system L, and to fire an excimer laser beam through an optics path that extends perpendicularly through the physician workstation enclosure 112, and then horizontally through an optical extension 114. The source of the laser beam is an excimer laser head found in a laser head enclosure 118. The optical extension 114 directs the excimer laser to the patient's eye as the patient lies on the patient bed 102, and also provides optics 116 for the physician to view the surgery before and while it takes place.

The optical extension 114 also includes an eye tracking system which partially uses the optical path extending through the physician workstation enclosure 112. The eye tracking system preferably employs a high speed video camera and dedicated electronics, and works in conjunction with the computer system to maintain the laser optics aligned with a desired point on the patient's eye.

The patient bed enclosure 100 also includes a foot rest 117 for the physician to use during surgery. This foot rest 117 further includes two foot switches 119 and 121, which control the vacuum and power to a microkeratome in an automated lamellar keratoplasty (ALK) system used in a LASIK procedure. This is further discussed below in conjunction with FIG. 5.

Preferably, the eye tracking system also employs Transputer™ boards manufactured by INMOS Limited used in conjunction with a Transputer Frame Grabber™ manufactured by Parsytech, GmbH, installed in the computer system.

Figure 2B:
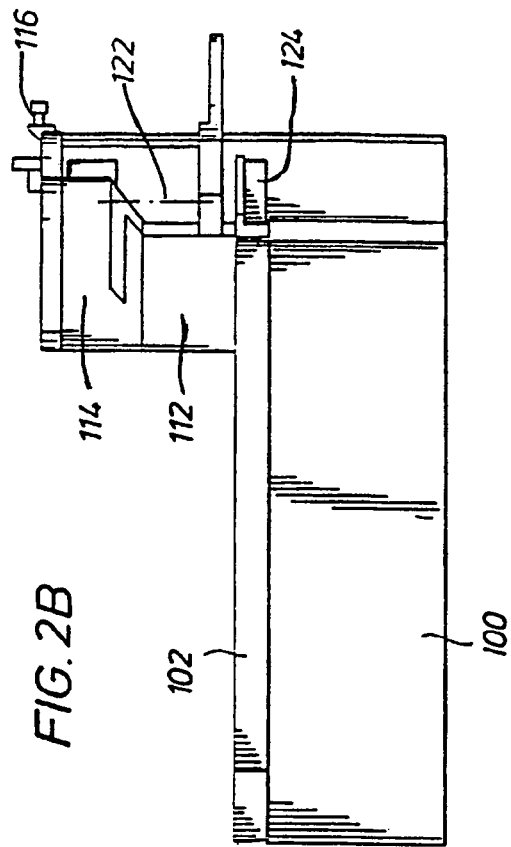
FIGS. 2A–C are top, side, and front views of the laser system according to the invention.
Figure 2A:
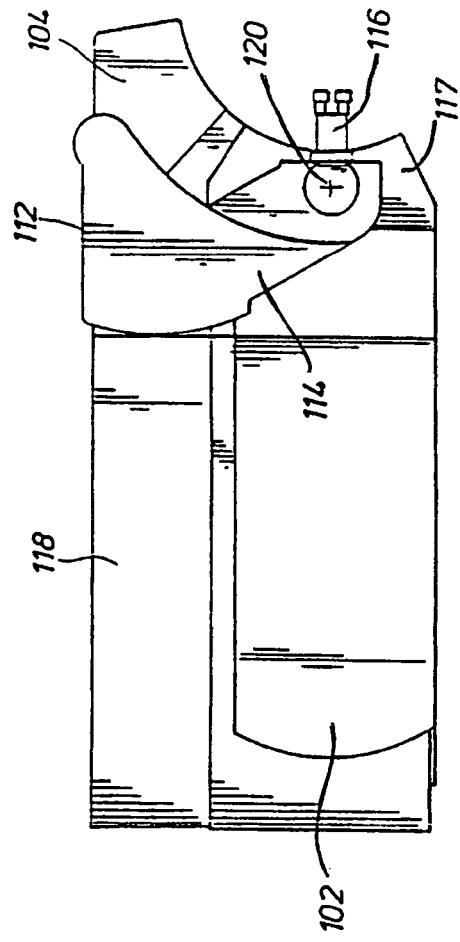
Figure 2C:
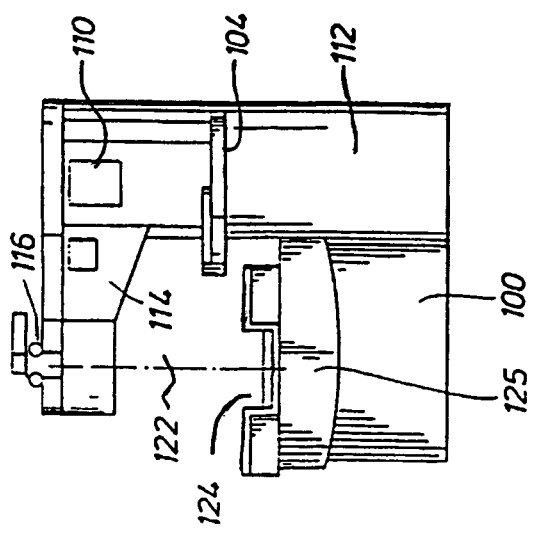

Turning to FIGS. 2A–C, shown are views of the system of FIG. 1. A top view in FIG. 2A illustrates how the optical extension 114 extends substantially over a head portion 124 of the patient bed 102. The physician then uses the optics 116 to observe the surgery as it takes place.

Also from this position, it is seen that adjacent to the patient bed 102 is the laser head housing 118. This laser head in the laser head housing 118 fires the laser beam, preferably a 193 nanometer excimer laser. This beam is fired parallel to the floor and then is reflected vertically up through the physician workstation enclosure 112, and then out through the optical extension 114. The laser beam is then reflected down into the patient's eye at a center point 120.

Turning to FIG. 2B, another view of the workstation is shown. From this view, a final beam path 122 is shown firing down from the optical extension 114 towards a head portion 124 of the bed 102. It is also seen that if a patient were to sit up, the patient could strike his or her head on the optical extension 114. In FIG. 2B, it is seen that the laser head 118 does not extend above the patient bed 102. This feature will be appreciated in conjunction with FIG. 3A discussed below.

Turning to FIG. 2C, shown is an end view, again showing the beam path 122 at which the excimer laser will fire onto the head portion 124 of the bed 102. Also, it is seen that the height of the workstation platform 104 is set so that the physician is provided easy access to both the keyboard 106 and to the patient's head, which is resting in the head portion 124 of the patient bed 102. FIG. 2C also shows a patient bed adjustment platform 125, which is part of the patient bed enclosure 125. This adjustment platform 125 provides motorized control of the patient bed 102 in the x, y, and z axes through the controls 108.

Turning to FIG. 3A, shown is the patient bed 102 in its rotated position. The patient bed 102 rotates on a bearing 126, which firmly connects the patient bed 102 to the patient bed enclosure 100. The patient bed 102 position is adjusted by motors and pulleys 140, which provide x, y, and z axes control of the adjustment platform 125. Further, the patient bed 102 rotates over the laser head 118. Preferably, the patient bed rotates sufficient so that the head portion 124 of the patient bed 102 has rotated out from under the optical extension 114. The patient can then sit up without striking his or her head on the optical extension 114. Further, the patient bed 102 can preferably rotate up to 90°, so that a single clean room could be used for performing both laser and non-laser ophthalmic surgery. In this position, not shown, the doctor would operate on the patient's head located within a head portion 124 of the patient bed 102, but rotated 90° away from the physician workstation platform 104. Further, preferably an electric solenoid 127 electrically latches into a latching hole 128 on the patient bed 102, holding the patient bed 102 in place during surgery. By providing the laser head 118 below the surface of the patient bed 102, the patient bed 102 can rotate over it.

Three more views of the patient bed 102 and the patient bed enclosure 100 are shown in FIGS. 3B, 3C, and 3D. FIG. 3B is an end view from the perspective of the head portion 124 end of the patient bed 102, and shows that the patient bed 102 is mounted on rollers 129 and locked into place with stops 1130. In practice, the patient bed enclosure 100 forms a cover that encloses a gas bottle holding argon fluoride gas needed by the laser head, cooling components, and electronics needed by the entire system. This is further discussed below in conjunction with FIGS. 4A–C.

The patient bed enclosure 100 is rolled over those components in a direction 131 and then locked into place with the stops 130 before the system is operated.

FIG. 3C illustrates a left (from a patient's perspective) side view of the patient bed enclosure 100 and the patient bed 102.

FIG. 3D illustrates a bottom end view (from the patient's perspective) of the patient bed 102 and the patient bed enclosure 100. As can be seen, an additional recess 132 is formed to accommodate the laser head discussed below in conjunction with FIGS. 4A–C.

Given FIGS. 3A–D, it will be appreciated that there is an open space formed underneath the patient bed enclosure 100. This open space is used to enclose the material necessary for the laser system L to operate. By providing the patient bed enclosure 100 as the cover for these components, the patient bed 102 and the patient bed enclosure 100 can be easily rolled away from these components to allow easy access and service. At the same time, using this enclosed space is an advantage in surgical systems because clean room operating space is a scarce resource. Therefore, a smaller and more compact system provides advantages because it reduces then size of the clean room necessary.

Turning to FIGS. 4A–C, shown are block diagrams illustrating the arrangement of the components underneath the patient bed enclosure 100. Referring to FIG. 4A, shown is a gas bottle 200, electronics 202 for both providing power and for providing the computer system for the laser system L, and an internal laser head 204. AC power components are provided in the open space 203 left of the electronics 202. The electronics 202 include the computer system, the bed power supplies, and other system electronics, such as transformers and interface circuits. The internal laser head 204 is enclosed by the laser head enclosure 118, and forms a laser beam, preferably a 193 nanometer excimer laser beam that fired a left to right in reference to the diagram of FIG. 4A The laser head 204 preferably includes an integral 30K volt power supply. Further included are various cooling components 206.

Referring to the end view of FIG. 4B, it is seen that the gas bottle 200 is mounted on rollers 208 for easy replacement of the gas bottle 200 after the patient bed enclosure 100 is rolled out of the way. Further, it is seen that the electronics 202 include a portion that surrounds the gas bottle 200, thereby more efficiently using the space. Again, the laser head 204 is shown, with beam egress points 210 and 212 for providing the excimer laser beam which is then reflected transversely through the optical extension 114, which forms the final beam directing portion. That final beam directing portion then redirects the laser beams into the patient's eye. Further, the final beam direction portion includes optics necessary to adjust the position that the excimer laser beam strikes the patient's eye. Also, an aiming laser is preferably provided in the optical extension 114 colinearly aligned with the excimer laser. This preferably includes two aiming mirrors, one for each axis.

Turning to FIG. 4C, a side view from the perspective as FIG. 3C is illustrated of the internal components. Again, it is seen how the electronics 202 wrap around the gas bottle 200.

Figure 5:
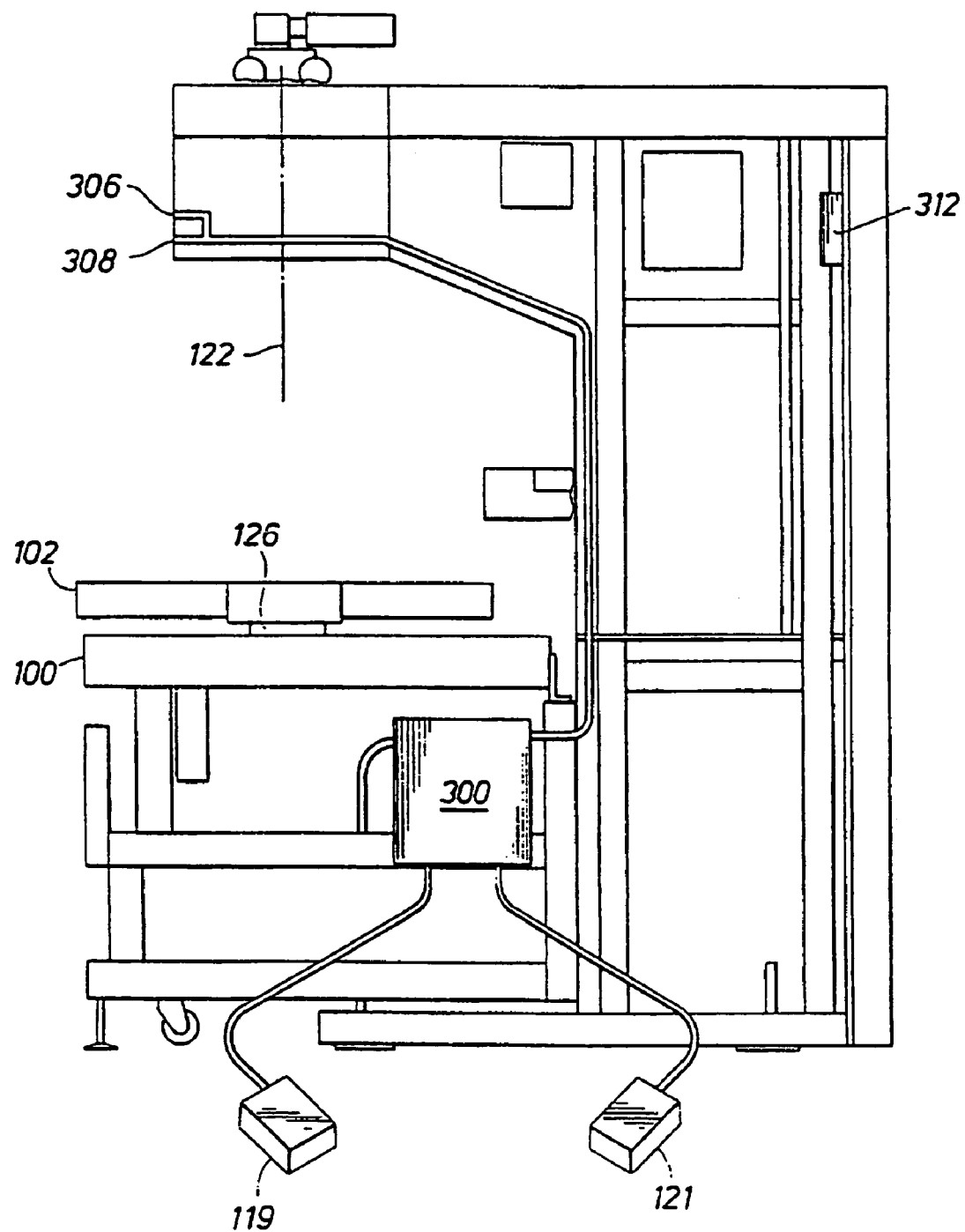
FIG. 5 is a front view of the internal components of the system of FIG. 1, further illustrating the incorporated automated lamellar keratoplasty (ALK) system for performing LASIK.

Turning to FIG. 5, yet another view is shown. In this case, an ALK, or automated lamellar keratoplasty system 300 is integrated into the laser system L. Automated lamellar keratoplasty is a system used to assist in a LASIK procedure, or a laser in situ keratomileusis procedure. This procedure requires a microkeratome, which preferably includes a vacuum port for providing suction for attachment to the eye and a power port for providing a high speed oscillating movement of the blade. Once a flap is taken from the patient's eye as the patient's head rests in the bed 124, the flap is pulled back and tissue underneath is excised, according to the technique described by Gholam Peyman in his previously incorporated U.S. patent.

Such systems, however, require monitoring and control, so preferably the two foot switches 117 and 119 are provided for the ALK system 300. These switches turn the vacuum on and off power the microkeratome. The vacuum and power for the ALK are provided integrally through the laser system L through two ports 306 and 308. Preferably, a nurse will be stationed adjacent to the doctor and attach the microkeratome when it is needed. The ports 306 and 308 can of course be located elsewhere on the laser system L, but their integral nature assists in the operation. Further, the ALK system is coupled to the electronics 202 for monitoring. For example, if the vacuum fails, one would immediately wish to cease blade movement, because high speed blade movement is necessary to prevent binding with the lamellar flap as it is taken. Further, the ALK system can be further integrated and controlled through computer access via the computer system in the electronics 202. The computer system is preferably integrated to the electronics 202 and provides control for various systems, including the display 110, the control inputs 108, and the keyboard 106. Further, the computer system preferably controls the eye tracking system, the aiming system, the laser head 204 and the firing of the laser head 204. Further, the computer system preferably includes a remote disk drive slot 312, for example for the insertion of a preprogrammed shot pattern, such as that described in assignee's co-pending U.S. patent application Ser. No. 08/656,855 entitled "Distributed Laser Surgery System" and filed concurrently herewith.

The computer system can be further integrated with the automated lamellar keratoplasty system 300. The automated lamellar keratoplasty system 300 typically provides a vacuum pressure output signal, microkeratome voltage and current output signals, as well as control inputs. The computer system can both display the microkeratome voltage and current and vacuum pressure, and generate warning messages or disable both the power source within the automated lamellar keratoplasty system and the vacuum source within the automated lamellar keratoplasty system should there be a failure. Further, the computer system can be disposed between the automated lamellar keratoplasty system 300 and the foot switches 119 and 121, so that the computer system itself controls the automated lamellar keratoplasty system 300 responsive to the foot switches 119 and 121.

Further, using the keyboard 106, the user in such a situation could set the power level of the power source in the automated lamellar keratoplasty system 300 and the vacuum pressure of the vacuum source within the automated lamellar keratoplasty system 300 using feedback on the display 110 on a routine executing in the computer system of the electronics 202.

In view of the foregoing discussion and figures, it will be appreciated that the system provides a compact excimer laser surgery system with a rotatable bed for patient convenience and for non-excimer laser operation. Further, an integrated ALK system provides for the convenient performance of laser in situ keratomileusis.

Finally, arrangement of components underneath the patient bed enclosure and patient bed, their arrangement next to the laser head, reduces the space taken by the system, thus providing for the more efficient of clean room environments.

The foregoing disclosure and description of the invention are illustrative and explanatory thereof and various changes in the size, shape, materials, components, circuit elements, wiring connections and contacts, as well as in the details of the illustrated circuitry and construction and method of operation may be made without departing from the spirit of the invention.

What is claimed is:

1. A compact excimer laser surgery system comprising:
    a patient bed enclosure with a patient surface and a patient height, said patient bed enclosure surrounding an open space, wherein the patient surface is rotatable on an axis that is generally parallel to a final laser beam path;
    a laser disposed in said open space;
    an electronics package for providing computer control disposed in said open space;
    a laser head located adjacent to said patient at a height less than said patient height, said laser head being connected to said electronics package for receiving power.

2. The system of claim 1 further comprising an aiming system providing an optical path from said laser head, said aiming system disposed perpendicularly upwards from the laser head, transversely across from the laser head in an optical extension above the patient bed, the aiming system to provide the laser beam substantially perpendicular towards the eye of the patient on the patient bed.

3. The system of claim 1 further including a laser gas container disposed in said open space and cooling system components disposed in said open space adjacent to said laser gas container.

4. The system of claim 3, wherein power components are disposed between said cooling system components and said electronics.

5. The system of claim 1, wherein said patient bed is mounted on a rollers with stops, allowing said patient bed to be rolled away to provide access to said open space in said patient bed enclosure.

6. The system of claim 1, wherein said patient bed is rotatable over a range up to 90 degrees.

* * * * *